(12) United States Patent
Solano Montenegro et al.

(10) Patent No.: US 12,076,015 B2
(45) Date of Patent: *Sep. 3, 2024

(54) HEMOSTASIS CLIP SHORT SYSTEM

(71) Applicant: Boston Scientific Scimed, Inc., Maple Grove, MN (US)

(72) Inventors: Esteban Solano Montenegro, Heredia (CR); Daniel Eduardo Mata Barrantes, San Isidro (CR); Jose Pablo Nunez Corella, San Jose (CR)

(73) Assignee: Boston Scientific Scimed, Inc., Maple Grove, MN (US)

( * ) Notice: Subject to any disclaimer, the term of this patent is extended or adjusted under 35 U.S.C. 154(b) by 98 days.

This patent is subject to a terminal disclaimer.

(21) Appl. No.: 17/936,726

(22) Filed: Sep. 29, 2022

(65) Prior Publication Data

US 2023/0014853 A1 Jan. 19, 2023

Related U.S. Application Data

(63) Continuation of application No. 16/898,130, filed on Jun. 10, 2020, now Pat. No. 11,484,314.

(Continued)

(51) Int. Cl.
*A61B 17/08* (2006.01)
*A61B 17/00* (2006.01)

(52) U.S. Cl.
CPC ........ *A61B 17/083* (2013.01); *A61B 17/0057* (2013.01); *A61B 2017/00473* (2013.01);

(Continued)

(58) Field of Classification Search
CPC .............. A61B 17/083; A61B 17/0057; A61B 2017/00473; A61B 2017/00584; A61B 2017/00818
See application file for complete search history.

(56) References Cited

U.S. PATENT DOCUMENTS

| | | | | |
|---|---|---|---|---|
| 5,520,701 | A * | 5/1996 | Lerch | A61B 17/122 606/151 |
| 6,991,634 | B2 * | 1/2006 | Sugiyama | A61B 17/122 606/151 |

(Continued)

FOREIGN PATENT DOCUMENTS

| | | |
|---|---|---|
| CN | 102065780 | 5/2011 |
| CN | 109640841 | 4/2019 |

*Primary Examiner* — Alexander J Orkin
(74) *Attorney, Agent, or Firm* — Fay Kaplun & Marcin, LLP

(57) ABSTRACT

A device includes a capsule along with first and second clip arms, proximal ends of which are received within the channel so that the first and second clip arms are movable relative to one another between an open configuration and a closed configuration. A deployment mechanism includes a tension member connected to a proximal end of the first and second arms, a yoke releasably coupled to the tension member and longitudinally movable relative to the capsule to move the first and second arms between the open and closed configurations. The tension member and yoke are configured to separate from one another in response to a predetermined proximal force relative to the tension member. A locking mechanism is coupled to the deployment mechanism and is configured to engage the capsule to lock the one-piece clipping element in the closed configuration, when the yoke is separated from the tension member.

20 Claims, 4 Drawing Sheets

Related U.S. Application Data

(60) Provisional application No. 62/863,016, filed on Jun. 18, 2019.

(52) U.S. Cl.
 CPC ............ *A61B 2017/00584* (2013.01); *A61B 2017/00818* (2013.01)

(56) References Cited

U.S. PATENT DOCUMENTS

| | | | |
|---|---|---|---|
| 11,484,314 B2* | 11/2022 | Solano Montenegro ................... A61B 17/083 |
| 2002/0045909 A1* | 4/2002 | Kimura ............... A61B 17/083 | 606/151 |
| 2003/0069592 A1* | 4/2003 | Adams ............... A61B 17/1227 | 606/142 |
| 2005/0049618 A1* | 3/2005 | Masuda ............. A61B 17/1285 | 606/151 |
| 2005/0080440 A1* | 4/2005 | Durgin ................ A61B 17/122 | 606/151 |
| 2005/0143767 A1* | 6/2005 | Kimura .................. A61B 50/30 | 606/158 |
| 2008/0140089 A1* | 6/2008 | Kogiso ............. A61B 17/1285 | 606/142 |
| 2009/0105533 A1* | 4/2009 | Fujita ................ A61B 17/1227 | 600/104 |
| 2010/0016873 A1* | 1/2010 | Gayzik ............. A61B 17/1227 | 606/151 |
| 2013/0027295 A1* | 1/2013 | Kuriya .................. G06V 40/23 | 345/156 |
| 2014/0088616 A1 | 3/2014 | Clerc et al. | |
| 2018/0140300 A1* | 5/2018 | Randhawa ......... A61B 17/1285 | |
| 2018/0153552 A1 | 6/2018 | King et al. | |

* cited by examiner

HEMOSTASIS CLIP SHORT SYSTEM

PRIORITY CLAIM

The present application is a Continuation of U.S. patent application Ser. No. 16/898,130 filed on Jun. 10, 2020, now U.S. Pat. No. 11,484,314; which claims priority to U.S. Provisional Patent Application Ser. No. 62/863,016 filed Jun. 18, 2019. The disclosures of the above application(s)/patent(s) are incorporated herewith by reference.

FIELD

The present disclosure relates to endoscopic devices and, in particular, relates to endoscopic clipping devices for treating tissue along the gastrointestinal tract.

BACKGROUND

During endoscopic gastrointestinal (GI) procedures, the patient may be at risk of perforation of a wall of the GI tract, or may require closure of the GI tract wall as part of the procedure. Hemostasis clips may be used for hemostasis of, for example, mucosal/sub-mucosal defects, bleeding ulcers, arteries, polyps, diverticula, along with closure of luminal tract perforations. Depending on the size of the defect, multiple clips may be required.

SUMMARY

The present disclosure relates to a device for treating tissue, comprising a capsule extending longitudinally from a proximal end to a distal end and including a channel extending therethrough along with first and second clip arms, proximal ends of which are received within the channel so that the first and second clip arms are movable relative to one another between an open configuration and a closed configuration. A deployment mechanism including a tension member connected to a proximal end of the first and second clip arms, a yoke releasably coupled to the tension member and longitudinally movable relative to the capsule to move the first and second clip arms between the open and closed configurations. The tension member and yoke are configured to separate from one another to release the device from a proximal portion thereof, in response to a predetermined proximal force relative to the tension member. A locking mechanism is coupled to the deployment mechanism and including a pair of locking fingers configured to engage a corresponding locking feature of the capsule to lock the first and second clip arms in the closed configuration, when the yoke is separated from the tension member.

In an embodiment, the first and second clip arms may be defined via a one-piece clipping element extending from a first end to a second end and including a bend along a portion thereof, the bend extending along a midpoint of the one-piece clipping element so that a length of the first and second clip arms substantially correspond In an embodiment, a distal end of tension member may be connected to the proximal end of the clip arms via a pin extending diametrically across the distal end of the tension member and through a substantially rounded space formed at the proximal end of the clip arms via the bend along the one-piece clipping element.

In an embodiment, the locking mechanism may include a ring coupled to the distal end of the tension member via the pin, the pair of locking fingers extending proximally from the ring.

In an embodiment, the locking fingers may be biased radially outward and include locking structures extending from proximal ends thereof.

In an embodiment, the yoke may include a pair of overhangs constraining the proximal ends of the locking fingers against the yoke and preventing the locking structures from engaging the locking features of the capsule until the yoke is separated from the tension member.

In an embodiment, the capsule may have a length ranging from between approximately 7.5 mm to 8.5 mm.

In an embodiment, the first and second clip arms may be biased toward the open configuration so that, when the first and second clip arms are drawn proximally into the capsule, the first and second clip arms are constrained toward the closed configuration, and when the first and second clip arms are moved distally out of the capsule, the first and second clip arms are permitted to revert to their biased open configuration.

The present disclosure also relates to a clipping device, comprising a clip including a capsule extending longitudinally from a proximal end to a distal end and including a channel extending therethrough. Proximal ends of first and second clip arms are slidably received within the channel of the capsule to move the first and second clip arms relative to one another between an open configuration and a closed configuration. A deployment mechanism includes a tension member connected to a proximal end of the first and second clip arms. A yoke is releasably coupled to the tension member and is couplable to a control member, which is movable relative to the capsule to move the first and second clip arms between the open and closed configurations. The tension member and yoke are configured to separate in response to a predetermined proximal force relative to the tension member. A locking mechanism is coupled to the deployment mechanism and includes a pair of locking fingers configured to engage a corresponding locking feature of the capsule to lock the first and second clip arms in the closed configuration, when the yoke is separated from the tension member. A proximal portion is releasably coupled to the proximal end of the capsule so that, upon separation of the yoke from the tension member, the clip is released from the proximal portion and deployed in a body over the target tissue.

In an embodiment, the first and second clip arms may be defined via a one-piece clipping element extending from a first end to a second end and including a bend along a portion thereof, the bend extending along a midpoint of the one-piece clipping element so that a length of the first and second clip arms substantially correspond In an embodiment, a distal end of the tension member may be connected to the proximal end of the clip arms via a pin extending diametrically across the distal end of the tension member and through a substantially rounded space formed at the proximal end of the clip arms via the bend along the one-piece clipping element.

In an embodiment, the locking mechanism may include a ring coupled to the distal end of the tension member via the pin, the pair of locking fingers extending proximally from the ring.

In an embodiment, the locking fingers may be biased radially outward and include locking structures extending from proximal ends thereof.

In an embodiment, the yoke may include a pair of overhangs constraining the proximal ends of the locking fingers against the yoke and preventing the locking structures from engaging the locking features of the capsule until the yoke is separated from the tension member.

In an embodiment, the capsule may have a length ranging from between approximately 7.5 mm to 8.5 mm.

The present disclosure also relates to a method for treating target tissue. A clip device is inserted through a working channel of an endoscope to a target site within a body until a clip of the clip device extends distally past a distal end of the working channel. The clip device includes a capsule and a pair of clip arms, proximal ends of which are slidably received within the capsule. The clip device is moved between an open configuration and a closed configuration until a selected target tissue is gripped between the first and second ends of the one-piece clipping element, the first and second clip arms moved between the open and closed configurations via a control wire coupled to a yoke that is releasably coupled to a tension member connected to the first and second clip arms. The clip device is locked in the closed configuration, once the target tissue is gripped as desired, by applying a predetermined proximal force along the control member to separate the yoke from the tension member, which permits locking fingers of a locking mechanism to engage corresponding locking features of the capsule.

DETAILED DESCRIPTION

Figure 1:
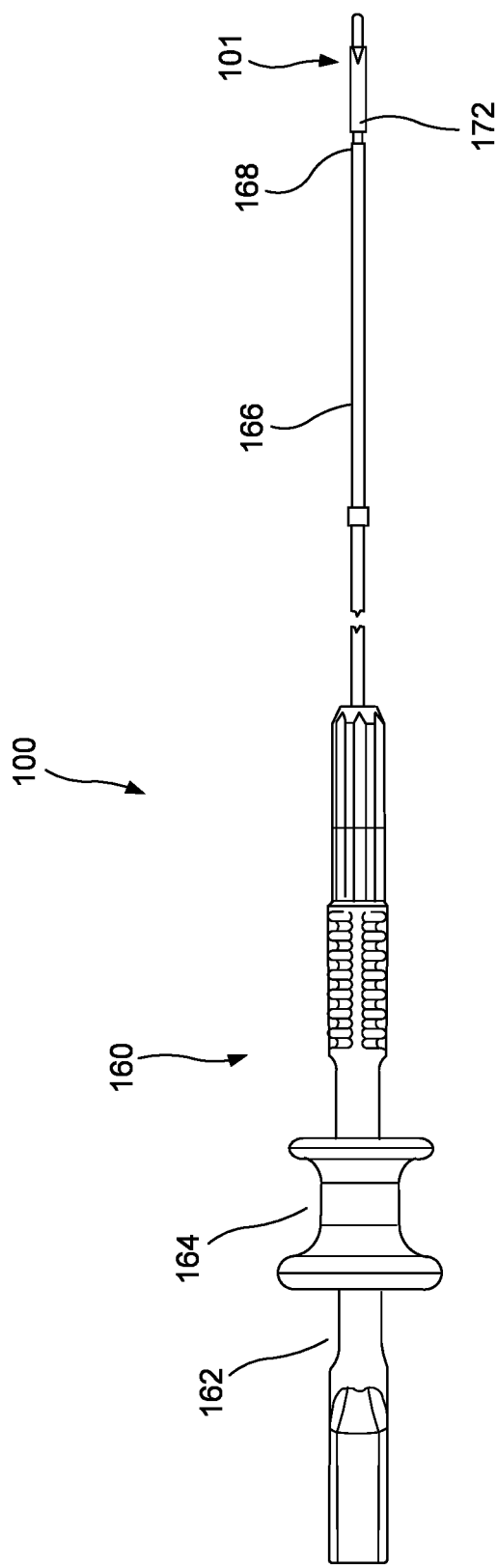
FIG. 1 shows a longitudinal side view of a device according to an exemplary embodiment of the present disclosure.
Figure 2:
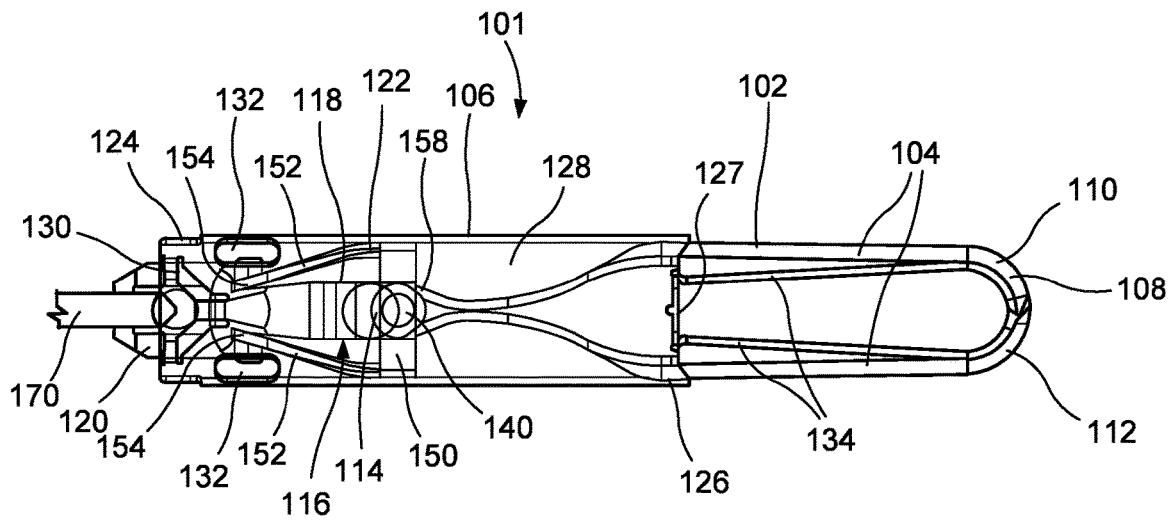
FIG. 2 shows a partially transparent longitudinal side view of a clip according to the device of FIG. 1.
Figure 3:
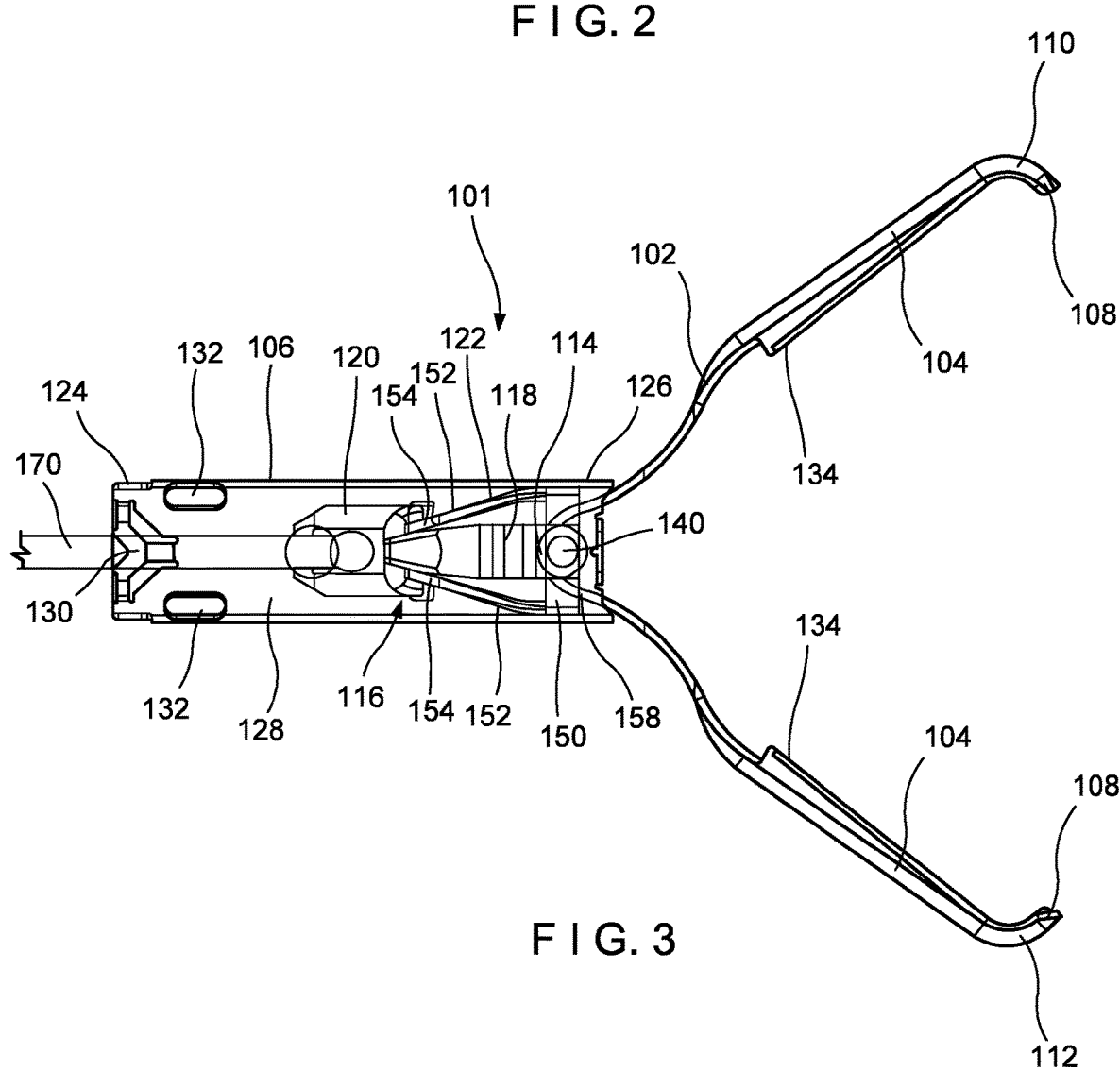
FIG. 3 shows another partially transparent longitudinal side view of the clip of FIG. 2, in an open configuration.
Figure 4:
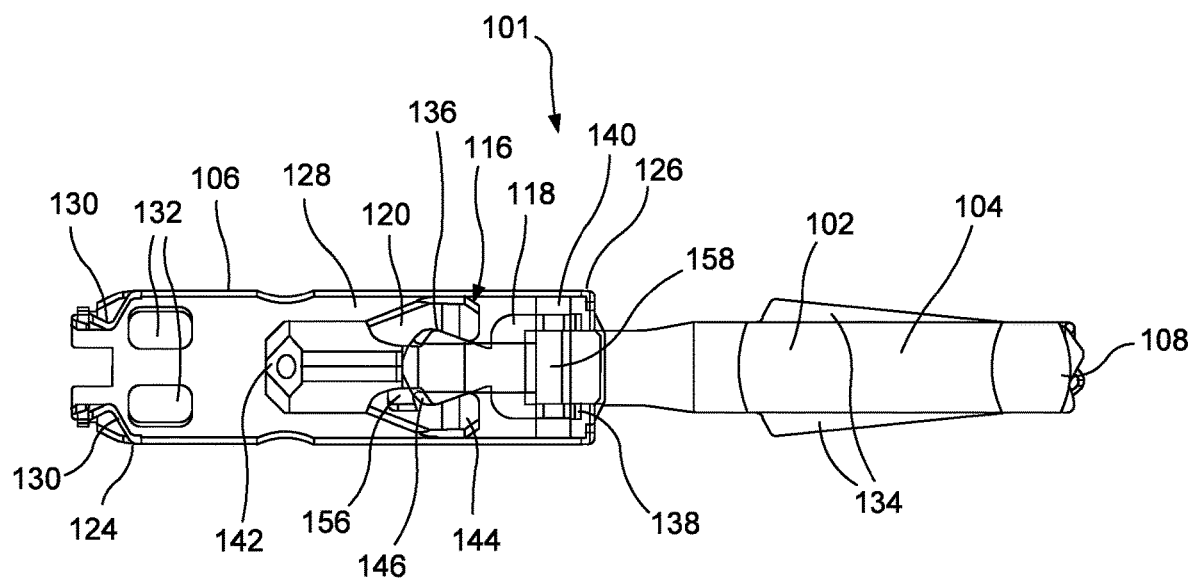
FIG. 4 shows another partially transparent longitudinal side view of the clip of FIG. 2, rotated 90 degrees about a longitudinal axis thereof and in the open configuration.
Figure 5:
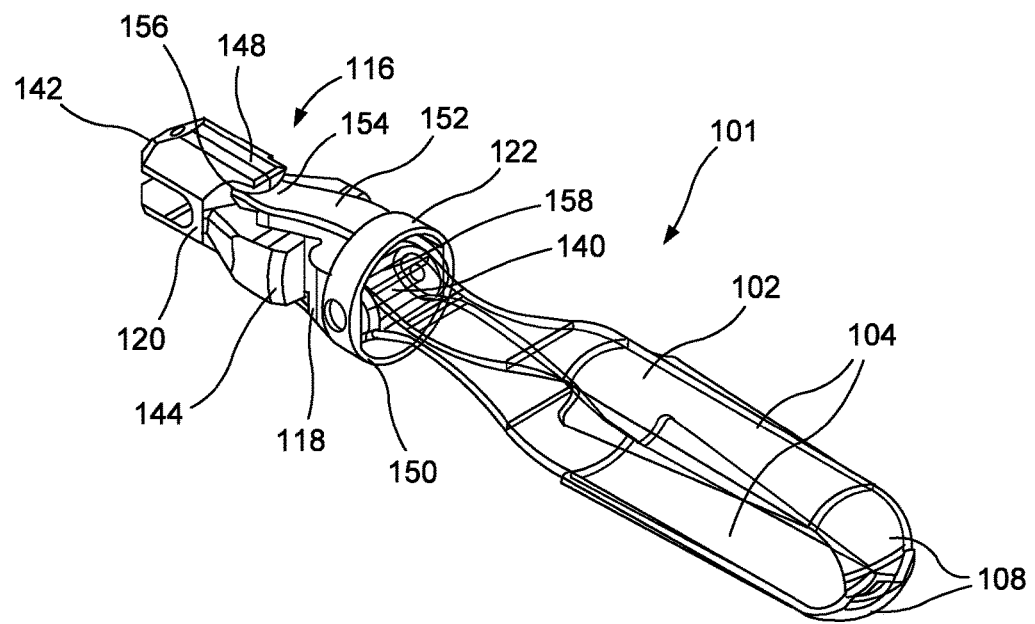
FIG. 5 shows a perspective view of a deployment mechanism, locking mechanism and clip arms of the clip of FIG. 2.
Figure 6:
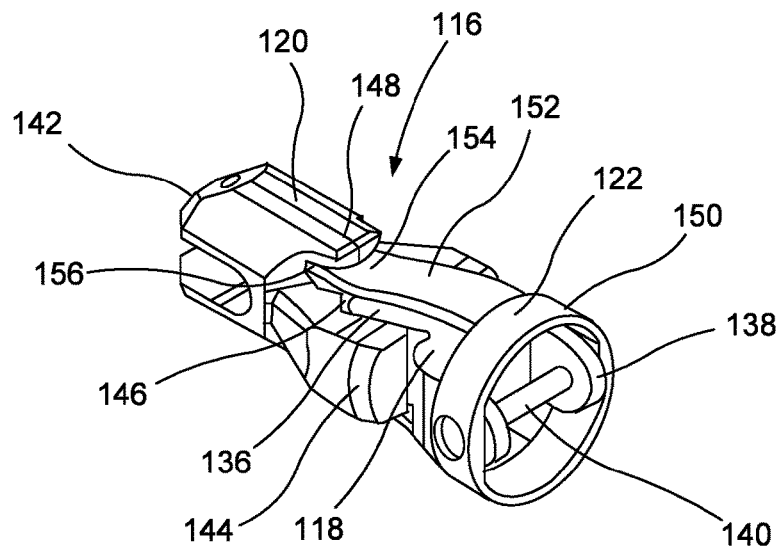
FIG. 6 shows a perspective view of a deployment mechanism and locking mechanism of the clip of FIG. 2.
Figure 7:
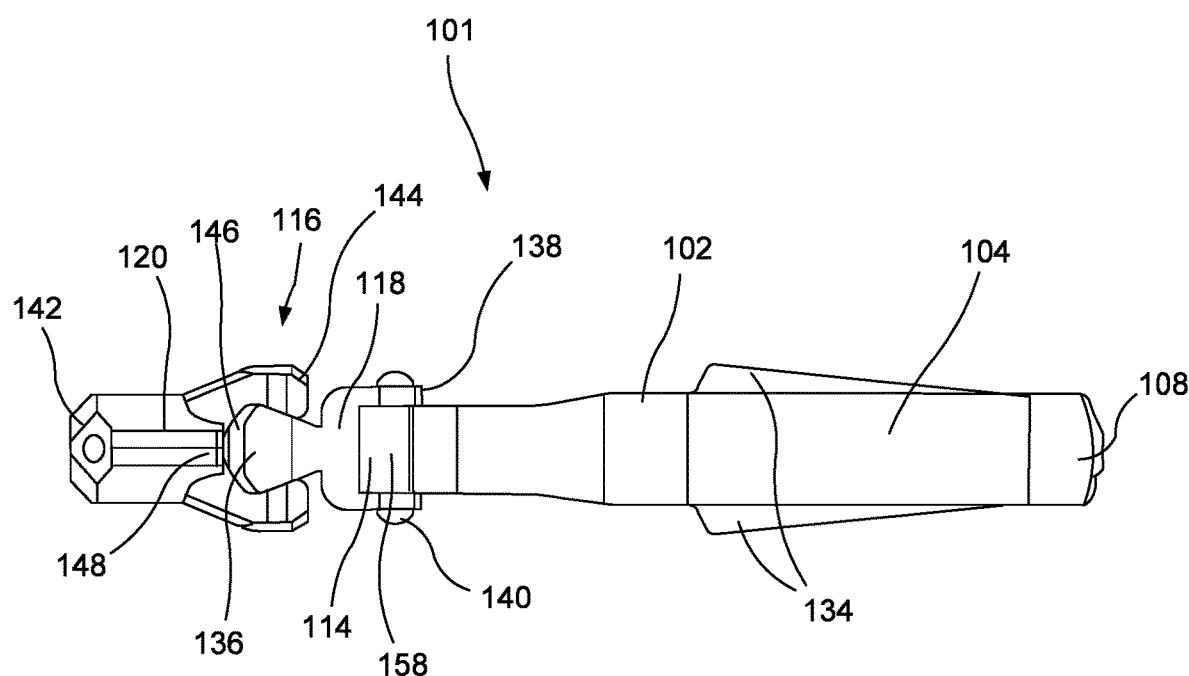
FIG. 7 shows a longitudinal side view of a deployment mechanism and clip arms of the clip of FIG. 2.

The present disclosure may be further understood with reference to the following description and the appended drawings, wherein like elements are referred to with the same reference numerals. The present disclosure is directed to an endoscopic clipping device for treating internal tissue perforations, defects and/or bleeds. In some embodiments, a shorter deployed clip may be preferred to improve visualization of the target site and to allow better maneuverability when placing multiple clips. Exemplary embodiments of the present disclosure describe a clip including clip arms defined via a one-piece element slidable within a capsule to move the clip between an open configuration and a closed configuration to clip target tissue, as desired. The one-piece element is connected to a separate deployment mechanism and locking mechanism to decrease a length of a deployed clip relative to other conventional clip designs which include capsules. It will be understood by those of skill in the art that the terms proximal and distal as used herein, are intended to refer to a direction toward and away from, respectively, a user of the device.

As shown in FIGS. 1-7, a clip device 100 according to an exemplary embodiment of the present disclosure comprises a clip 101 including a one-piece element 102 defining a pair of clip arms 104 received within a capsule 106 to move the clip arms 104 between an open configuration, in which distal ends 108 of the clip arms 104 are separated from one another, and a closed configuration, in which the distal ends 108 are drawn toward one another to grip tissue. In embodiments, the one-piece element 102 extends from a first end 110 to a second end 112 and is bent, for example, at a joint or midpoint 114 to define the clip arms 104. The midpoint 114 is connected to a deployment mechanism 116 including a tension member 118 and a yoke 120, which are slidably received within the capsule 106 to move the clip arms 104 between the open and the closed configuration.

A locking mechanism 122 is coupled to the one-piece element 102 and the deployment mechanism 116 so that, when the clip 101 is deployed over target tissue in a body, the clip 101 is locked in the closed configuration. In one embodiment, as shown in FIG. 1, the clip 101 is releasably coupled to an elongated proximal portion 160 of the device 100 sized to facilitate insertion of the clip 101 through a working channel of an endoscope to a target site within the body while a proximal end remains outside the body accessible to a user. The proximal portion 160 may include, for example, a handle member 162 including actuators 164 enabling a user to control movement and deployment of the clip 101 and a flexible shaft 166 extending distally from the handle member 162 to the clip 101, a distal end 168 of the flexible shaft 166 being releasably coupled to the clip 101 via, for example, a bushing 172. The user manipulates the actuators 164 to move a control member 170 that extends from the handle member 162, through the flexible shaft 166 to connect to the clip arms 104 to control movement of the clip arms 104 between the open and closed configurations.

The capsule 106 extends from a proximal end 124 to a distal end 126 and includes a channel 128 extending therethrough. In one embodiment, the proximal end 124 is configured to be releasably coupled to the proximal portion of the device via tabs 130 at the proximal end 124 of the capsule 106, which may be crimped radially inward to engage a corresponding portion of the proximal portion. The capsule 106 also includes, for example, locking features formed in a capsule wall such as, for example, locking windows 132 that extend laterally through the capsule wall for engaging a portion of the locking mechanism 122, as will be described in further detail below.

In one embodiment, the capsule 106 may have a length ranging from between 7.5 mm to 8.55 mm. The capsule 106 of this embodiment is substantially shorter than capsule lengths of some conventional clips, which may have lengths ranging from between 12.5 mm to 13.5 mm. It will be understood by those of skill in the art that the one-piece design of the clip arms 104 and the separate locking mechanism 122, which will be described in further detail below, permits the capsule 106 to have a shorter length relative to some existing clips without sacrificing an opening width of the clip arms 104.

As described above, the clip arms 104 are formed from a one-piece element 102 which extends along a length from the first end 110 to the second end 112 and is bent at, for example, the midpoint 114 so that the clip arms 104 extend along a portion of a length extending from opposite sides of the midpoint 114, e.g., proximal of the first and second ends 110, 112. Thus, the first and second ends 110, 112 of the one-piece element 102 correspond to the distal ends 108 of the clip arms 104. The midpoint 114 is connected to the deployment mechanism 116 which is slidably received within the channel 128 of the capsule 106 so that the clip arms 104 are movable between the open and the closed configurations.

In one embodiment, the clip arms 104 are biased toward the open configuration so that, when advanced distally out of the capsule 106, the clip arms 104 move apart from one another into the open configuration under their natural bias. When the arms 104 are drawn proximally into the capsule 106, the clip arms 104 are constrained by the wall of the capsule 106 and drawn together into the closed position with the distal ends 108 adjacent one another. Those skilled in the art will understand that any number of other mechanisms for opening and closing the clip arms 104 may be employed. It will also be understood by those of skill in the art that although the exemplary embodiments show and describe a one-piece element 102 including a bend to form clip arms 104, in an alternative embodiment, proximal ends of clip arms may be attached to one another such that the proximal ends are connectable to the tension member 118.

The clip arms 104 of this embodiment also include engaging features 134 extending therefrom and configured to engage a portion of the capsule 106 so that, when the engaging features 134 engage the capsule 106, the clip arms 104 are prevented from being moved further proximally into the capsule 106. In one embodiment, the engaging features 134 extend laterally outward from portions of the clip arms 104 so that portions of the clip arms 104 distal of the engaging features 134 have a greater width than portions of the clip arms 104 proximal of the engaging features 134. The portions of the clip arms 104 extending proximal of the engaging features 134 are sized to permit these portions of the clip arms 104 to be drawn proximally into the capsule 106.

As the proximal portions of the clip arms 104 are drawn proximally into the capsule 106, the engaging features 134 abut a portion of a distal face 127 of the capsule 106 preventing the clip arms 104 from being drawn further proximally into the capsule 106. The engaging features 134 are positioned along the length of the clip arms 104 so that, at the point where the engaging features 134 have engaged the capsule 106, the clip arms 104 have been drawn sufficiently proximally into the capsule 106 to draw the clip arms 104 together into the closed configuration. In one example, the engaging features 134 are configured as wings extending laterally from longitudinal edges of the clip arms 104.

The tension member 118 extends from a proximal end 136 configured to be releasably coupled to the yoke 120 to a distal end 138 attached to the midpoint 114 of the one-piece element 102 via, for example, a pin 140. In one embodiment, the distal end 138 extends over the midpoint 114 such that the pin 140, which extends diametrically across the distal end 138, is received within a substantially rounded space at a proximal end 158 of the clip arms 104 defined by the bend of the one-piece element 102 at the midpoint 114. In other words, the pin 140 extends immediately distal of the midpoint 114 so that the pin 140 extends between the pair of arms 104 along an interior surface of the one-piece element 102 along the bend at the midpoint 114. The tension member 118 and the pin 140 are connected to the one-piece element 102 such that longitudinal movement of the tension member 118 relative to the capsule 106 correspondingly moves the clip arms 104 relative to the capsule 106. The proximal end 136 of the tension member 118 is sized and shaped to engage a correspondingly sized and shaped portion of the yoke 120. In one embodiment, the proximal end 136 includes a substantially C-shaped protrusion.

The yoke 120 extends from a proximal end 142 configured to be connected to a control member such as, for example, a pull wire to a distal end 144 configured to releasably engage the proximal end 136 of the tension member 118. In one embodiment, the distal end 144 included a substantially C-shaped recess 146 sized and shaped to receive the C-shaped protrusion of the proximal end 136. The proximal end 136 of the tension member 118 and the distal end 144 of the yoke 120 are configured to disengage one another when subject to a predetermined force as will be described in more detail below.

In one embodiment, a width along at least a portion of the yoke 120 substantially corresponds to a width (e.g., diameter) of the channel 128 of the capsule 106 so that, when the yoke 120 is positioned within the proximal end 124 of the capsule 106, the yoke 120 engages the tabs 130 to move the tabs 130 radially outward, out of engagement with the proximal portion of the device. The yoke 120 also includes a pair of overhangs 148 extending distally from a portion thereof. As will be described in further detail below, the overhangs 148 are configured to constrain proximal ends 154 of locking arms 152 of the locking mechanism 122 so that the locking arms 154 are prevented from engaging the locking features 134 of the capsule 106 until the clip 101 has been deployed over target tissue.

The locking mechanism 122 is attached to the tension member 118 and, as described above, includes locking arms 152 that are constrained by the yoke 120 until the clip 101 is deployed. In one embodiment, the locking mechanism 122 includes a ring 150 and a pair of locking arms 152 extending proximally from the ring 150. The ring 150 is attached to the tension member 118 via the same pin 140 that connects the tension member 118 to the clip arms 104. In particular, the pin 140 extends diametrically across the ring 150 so that the ring 150 extends about both the distal end 138 of the tension member 118 and the proximal end 158 of the clip arms 104.

The locking arms 152 extend proximally from the opposing sides of the ring 150 to the proximal ends 154 and, in one embodiment, are biased radially outward. The ring 150 is connected to the tension member 118 so that the locking arms 152 extend along opposing sides of the tension member 118 to be constrained via the overhangs 148 of the yoke 120. The proximal ends 154 of the locking arms 152 include locking structures 156 extending therefrom so that, when the proximal ends 154 are permitted to revert to their biased configuration, the locking structures 156 engage the locking features 132 of the capsule 106. In one embodiment, the locking structures 156 are configured as locking tabs extending from the proximal ends 154 to engage locking windows 132 of the capsule 106 when the proximal ends 154 are released from the overhangs 148. As will be described in further detail below, the proximal ends 154 are released and permitted to revert to their radially outwardly biased configuration when the predetermined force is exerted on the yoke 120 to separate the yoke 120 from the tension member 118.

According to an exemplary method, the clip 101 of the clip device 100 is inserted to a target site within the body via, for example, a working channel of an endoscope. The clip 101 is inserted through the working channel in the closed configuration so that the clip arms 104 do not damage in interior of the working channel. Once the clip 101 has reached the target site, the clip arms 104 are moved distally relative to the capsule 106 extending distal portions of the clip arms 104 out of the capsule 106 and freeing the clip arms 104 to move apart under their natural bias toward the open configuration so that target tissue may be received between the clip arms 104. The clip 101 may be repeatedly moved between the open and closed configurations until a target portion of tissue is positioned between the clip arms 104 as desired. The user then draws the clip arms 104 proximally into capsule 106 so that, as the clip arms 104 are drawn into the capsule 106, the clip arms 104 are drawn toward one another to grip the target tissue between the distal ends 108 of the clip arms 104. As described above, the clip 101 may be moved between the open and closed configurations via movement of, for example, the control member 170 coupled to the yoke 120.

When the user is satisfied that the clip 101 is in a desired position gripping the target tissue, the user applies increasing proximally directed force to the control member 170 after the engaging features 134 have engaged the capsule 106, as described above, until the predetermined force is pulling the yoke 120 proximally away from the tension member 118 so that they disengage from one another. As the yoke 120 is separated from the tension member 118, the proximal ends 154 of the locking mechanism 122 of the clip arms 104 are released from the overhangs 148 of the yoke 120, freeing the proximal ends 154 to spring toward their radially outwardly biased configuration until the locking tabs 156 engage the locking windows 132 of the capsule 106, thereby locking the clip 101 in the closed configuration.

The yoke 120 may then be drawn further proximally relative to the capsule 106 (e.g., via the control member connected thereto) until a portion of the yoke 120 having a width corresponding to the channel 128 of the capsule 106 is positioned within the proximal end 124 of the capsule 106, urging the radially inwardly crimped tabs 130 radially outward, out of engagement with, for example, the bushing 172 of the proximal portion 160 of the device 100 and separating the clip 101 from the proximal portion 160. Thus, the clip 101 remains clipped over the target tissue while the proximal portion 160 may be removed from the body. In one embodiment, upon separation of the clip 101 from the proximal portion 160, the tabs 130 revert to their radially inwardly crimped configuration so that the yoke 120, although separated from the tension member 118, remains attached to the proximal end 124 of the capsule 106.

In this embodiment, a further proximal force exerted on the control member 170 separates the control member from the yoke 120, leaving the clip 101 in the body and allowing the proximal portion 160 of the device 100, including the control member 170, to be removed therefrom. According to another embodiment, upon separation of the capsule 106 from the proximal portion 160, the yoke 120 may be drawn proximally out of the capsule 106 so that the clip 101 remains within the body, clipped over the target tissue, while the proximal portion 160 and the yoke 120 may be removed from the body.

It will be apparent to those skilled in the art that various modifications may be made in the present disclosure, without departing from the scope of the disclosure.

What is claimed is:

1. A device for treating tissue, comprising:
a clip including a capsule extending longitudinally from a proximal end to a distal end and including a channel extending therethrough, the clip further including a one-piece clipping element defining a pair of clip arms, proximal ends of which are received within the channel so that the first and second clip arms are movable relative to one another between an open configuration and a closed configuration;
a deployment mechanism including a tension member connected to the proximal ends of the first and second clip arms, a yoke releasably coupled to the tension member and longitudinally movable relative to the capsule to move the first and second clip arms between the open and closed configurations, the tension member and yoke configured to separate from one another to release the clip from a proximal portion of the device, in response to a predetermined proximal force applied to the tension member; and
a locking mechanism coupled to the one-piece clipping element and to the deployment mechanism, the locking mechanism including a pair of locking arms configured to engage a corresponding locking feature of the capsule to lock the first and second clip arms in the closed configuration when the yoke is separated from the tension member.

2. The device of claim 1, wherein the locking mechanism is separate from the one-piece clipping element.

3. The device of claim 1, wherein the one-piece clipping element is separate from the deployment mechanism and the locking mechanism.

4. The device of claim 1, further comprising:
a pin,
wherein a distal end of the tension member is connected to the proximal end of the clip arms via the pin, the pin extending diametrically across the distal end of the tension member and through a substantially rounded space formed at the proximal end of the clip arms.

5. The device of claim 4, wherein the one-piece clipping element extends from a first end to a second end and includes a bend along a portion thereof, the bend extending along a midpoint of the one-piece clipping element so that a length of the first and second clip arms substantially correspond.

6. The device of claim 5, wherein the substantially rounded space is formed at the proximal end of the clip arms via the bend along the one-piece clipping element.

7. The device of claim 6, wherein the locking mechanism includes a ring coupled to the distal end of the tension member via the pin, the pair of locking arms extending proximally from the ring.

8. The device of claim 7, wherein the locking arms are biased radially outward and include locking structures extending from proximal ends thereof.

9. The device of claim 8, wherein the yoke includes a pair of overhangs constraining the proximal ends of the locking arms against the yoke and preventing the locking structures from engaging the locking feature of the capsule until the yoke is separated from the tension member.

10. The device of claim 1, wherein the capsule has a length ranging from between approximately 7.5 mm to 8.5 mm.

11. The device of claim 1, wherein the first and second clip arms are biased toward the open configuration so that, when the first and second clip arms are drawn proximally into the capsule, the first and second clip arms are constrained toward the closed configuration, and when the first and second clip arms are moved distally out of the capsule, the first and second clip arms are permitted to revert to their biased open configuration.

12. A clipping device, comprising:
a clip including a capsule extending longitudinally from a proximal end to a distal end and including a channel extending therethrough, the clip further including a one-piece clipping element defining first and second clip arms, proximal ends of which are slidably received within the channel of the capsule to move the first and second clip arms relative to one another between an open configuration and a closed configuration;

a deployment mechanism including a tension member connected to the proximal ends of the first and second clip arms, a yoke releasably coupled to the tension member and couplable to a control member, which is movable relative to the capsule to move the first and second clip arms between the open and closed configurations, the tension member and yoke configured to separate in response to a predetermined proximal force applied to the tension member;

a locking mechanism coupled to the deployment mechanism and including a pair of locking arms configured to engage a corresponding locking feature of the capsule to lock the first and second clip arms in the closed configuration when the yoke is separated from the tension member; and a proximal portion releasably coupled to the proximal end of the capsule so that, upon separation of the yoke from the tension member, the clip is released from the proximal portion and deployed in a body over a target tissue.

13. The device of claim 12, wherein the one-piece clipping element is separate from the deployment mechanism and the locking mechanism.

14. The device of claim 12, further comprising:

a pin, wherein a distal end of the tension member is connected to the proximal end of the first and second clip arms via the pin, the pin extending diametrically across the distal end of the tension member and through a substantially rounded space formed at the proximal end of the first and second clip arms.

15. The device of claim 14, wherein the one-piece clipping element extends from a first end to a second end and includes a bend along a portion thereof, the bend extending along a midpoint of the one-piece clipping element so that a length of the first and second clip arms substantially correspond.

16. The device of claim 15, wherein the substantially rounded space is formed at the proximal end of the first and second clip arms via the bend along the one-piece clipping element.

17. The device of claim 16, wherein the locking mechanism includes a ring coupled to the distal end of the tension member via the pin, the pair of locking arms extending proximally from the ring.

18. The device of claim 17, wherein the locking arms are biased radially outward and include locking structures extending from proximal ends thereof.

19. The device of claim 18, wherein the yoke includes a pair of overhangs constraining the proximal ends of the locking arms against the yoke and preventing the locking structures from engaging the locking feature of the capsule until the yoke is separated from the tension member.

20. The device of claim 12, wherein the first and second clip arms are biased toward the open configuration so that, when the first and second clip arms are drawn proximally into the capsule, the first and second clip arms are constrained toward the closed configuration, and when the first and second clip arms are moved distally out of the capsule, the first and second clip arms are permitted to revert to their biased open configuration.

* * * * *